(12) United States Patent
Lauryssen et al.

(10) Patent No.: US 8,298,236 B2
(45) Date of Patent: *Oct. 30, 2012

(54) CERVICAL BONE PREPARATION TOOL AND IMPLANT GUIDE SYSTEMS

(75) Inventors: Carl Lauryssen, Beverly Hills, CA (US); James Kelly, N. Easton, MA (US); Thomas V. Doherty, Latham, NY (US)

(73) Assignee: DePuy Spine, Inc., Raynham, MA (US)

( * ) Notice: Subject to any disclaimer, the term of this patent is extended or adjusted under 35 U.S.C. 154(b) by 486 days.

This patent is subject to a terminal disclaimer.

(21) Appl. No.: 12/579,663

(22) Filed: Oct. 15, 2009

(65) Prior Publication Data

US 2010/0036442 A1   Feb. 11, 2010

Related U.S. Application Data

(63) Continuation of application No. 10/904,598, filed on Nov. 18, 2004.

(51) Int. Cl.
*A61F 2/46* (2006.01)
(52) U.S. Cl. .................................................. 606/86 R
(58) Field of Classification Search ............... 606/86 R, 606/96, 104; 600/185, 190, 200, 211, 213, 600/215, 228, 239, 240, 242, 243
See application file for complete search history.

(56) References Cited

U.S. PATENT DOCUMENTS

| | | | |
|---|---|---|---|
| 1,831,813 A * | 11/1931 | Levedahl | 408/81 |
| 1,908,010 A | 5/1933 | Cameron | |
| 2,466,023 A | 4/1949 | Griffin | |
| 3,867,932 A | 2/1975 | Huene | |
| 4,005,527 A | 2/1977 | Wilson et al. | |
| 4,341,206 A | 7/1982 | Perrett et al. | |
| 4,450,834 A | 5/1984 | Fischer | |
| 4,502,475 A | 3/1985 | Weigle et al. | |
| 4,686,972 A | 8/1987 | Kurland | |
| 4,817,587 A | 4/1989 | Janese | |
| 4,883,048 A | 11/1989 | Purnell et al. | |
| 4,896,663 A | 1/1990 | Vandewalls | |
| 4,969,781 A * | 11/1990 | Fahrner et al. | 408/79 |
| 5,056,523 A | 10/1991 | Hotchkiss, Jr. et al. | |

(Continued)

FOREIGN PATENT DOCUMENTS

EP   1348383 A1   10/2003

(Continued)

OTHER PUBLICATIONS

European Search Report, Application No. EP05813816, Issued May 19, 2009, 11 pages.

(Continued)

*Primary Examiner* — Nicholas Woodall
(74) *Attorney, Agent, or Firm* — Nutter McClennen & Fish LLP

(57) ABSTRACT

Disclosed herein are various tools and devices for use in spinal surgery. In one embodiment, a spinal guide device is provided having a guide member with a positioning element that is adapted to engage a portion of a vertebra to position the guide member relative to the vertebra. The guide member can also include a retractor guide that is adapted to guide a retractor therethrough to retract tissue adjacent to the distal end of the guide member. Various tissue retractors, bone preparation tools, and spinal implants are also disclosed.

19 Claims, 13 Drawing Sheets

U.S. PATENT DOCUMENTS

| | | |
|---|---|---|
| 5,180,381 A | 1/1993 | Aust et al. |
| 5,190,548 A | 3/1993 | Davis |
| 5,303,694 A | 4/1994 | Mikhail |
| 5,320,626 A | 6/1994 | Schmieding |
| 5,409,493 A | 4/1995 | Greenberg |
| 5,423,826 A | 6/1995 | Coates et al. |
| 5,507,801 A | 4/1996 | Gisin et al. |
| 5,538,424 A | 7/1996 | Gelb |
| 5,558,622 A | 9/1996 | Greenberg |
| 5,603,713 A | 2/1997 | Aust et al. |
| 5,676,666 A | 10/1997 | Oxland et al. |
| 5,741,267 A | 4/1998 | Jorneus et al. |
| 5,755,721 A | 5/1998 | Hearn |
| 5,851,207 A | 12/1998 | Cesarone |
| 5,885,300 A | 3/1999 | Tokuhashi et al. |
| 5,941,706 A | 8/1999 | Ura |
| 5,951,561 A | 9/1999 | Pepper et al. |
| 6,063,088 A | 5/2000 | Winslow |
| 6,068,632 A | 5/2000 | Carchidi et al. |
| 6,146,383 A | 11/2000 | Studer et al. |
| 6,206,826 B1 | 3/2001 | Mathews et al. |
| 6,210,415 B1 | 4/2001 | Bester |
| 6,228,024 B1 | 5/2001 | Co et al. |
| 6,235,034 B1 | 5/2001 | Bray |
| 6,287,313 B1 | 9/2001 | Sasso |
| 6,332,887 B1 | 12/2001 | Knox |
| 6,342,056 B1 | 1/2002 | Mac-Thiong et al. |
| 6,342,057 B1 | 1/2002 | Brace et al. |
| 6,379,364 B1 | 4/2002 | Brace et al. |
| 6,416,517 B2 | 7/2002 | Harder et al. |
| 6,416,518 B1 | 7/2002 | DeMayo |
| 6,419,678 B1 | 7/2002 | Asfora |
| 6,520,907 B1 | 2/2003 | Foley et al. |
| 6,520,909 B1 | 2/2003 | Rankins |
| 6,562,046 B2 | 5/2003 | Sasso |
| 6,565,571 B1 | 5/2003 | Jackowski et al. |
| 6,692,503 B2 | 2/2004 | Foley et al. |
| 6,712,818 B1 | 3/2004 | Michelson |
| 6,827,722 B1 | 12/2004 | Schoenefeld |
| 7,226,453 B2 | 6/2007 | Chao et al. |
| 7,621,916 B2 | 11/2009 | Lauryssen et al. |
| 2001/0047172 A1 | 11/2001 | Foley et al. |
| 2002/0049444 A1 | 4/2002 | Knox |
| 2002/0082606 A1 | 6/2002 | Suddaby |
| 2002/0116006 A1 | 8/2002 | Cohen |
| 2002/0138079 A1 | 9/2002 | Cohen |
| 2002/0173794 A1 | 11/2002 | Happonen et al. |
| 2003/0018337 A1 | 1/2003 | Davis |
| 2003/0233098 A1 | 12/2003 | Markworth |
| 2003/0236447 A1 | 12/2003 | Ritland |
| 2004/0015174 A1 | 1/2004 | Null et al. |
| 2004/0092947 A1 | 5/2004 | Foley |
| 2004/0097929 A1 | 5/2004 | Branch et al. |
| 2004/0122432 A1 | 6/2004 | Chappuis |
| 2004/0204717 A1 | 10/2004 | Fanger et al. |
| 2004/0215196 A1 | 10/2004 | Suddaby |
| 2005/0273133 A1 | 12/2005 | Shluzas et al. |

FOREIGN PATENT DOCUMENTS

| | | |
|---|---|---|
| WO | 9322975 A1 | 11/1993 |
| WO | 0024327 A2 | 5/2000 |
| WO | 03007826 A1 | 1/2003 |
| WO | 03024344 A1 | 3/2003 |

OTHER PUBLICATIONS

Product Literature, by Synthes Spine, The Cervical Spine Locking Plate CSLP, 2000.

* cited by examiner

CERVICAL BONE PREPARATION TOOL AND IMPLANT GUIDE SYSTEMS

CROSS REFERENCE TO RELATED APPLICATIONS

This application is a continuation of U.S. patent application Ser. No. 10/904,598 filed Nov. 18, 2004 and entitled "Cervical Bone Preparation Tool And Implant Guide Systems," which is hereby incorporated by reference in its entirety.

BACKGROUND

The use of bone screws and plates for stabilization and immobilization of the cervical spine is common. One concern, however, with screws being implanted in the lateral masses of the cervical spine is that there are sensitive and/or important structures adjacent to the masses, which, because of their proximity to the implant, may be damaged by insertion or dislocation of screws. In the cervical spine, the vertebral arteries are positioned laterally beneath the lateral masses and comprise critical structures which should not be compromised. In addition, the facet joints, which provide natural coupling of sequential bones, together should also be avoided if possible. Avoidance of these bodies has been an important and ongoing concern with respect to posterior screw insertion. Current lateral mass screws provide little in the way of reasonable or practical solutions for ensuring proper screw insertion.

Accordingly, there remains a need for improved methods and devices for implanting bone screws in the spinal column, and in particular in the cervical spine.

SUMMARY

Disclosed herein are various tools and devices for use in spinal surgery. In one embodiment, a spinal guide device is provided having an elongate tubular guide member with proximal and distal ends. A handle can extend from the guide member on the guide device. The distal end of the guide member can include a positioning element that is adapted to engage a portion of a vertebra to position the guide member relative to the vertebra, and/or a retractor guide that is adapted to guide a retractor therethrough to retract tissue adjacent to the distal end of the guide member. The positioning element can have a variety of configurations, but in one embodiment it is a hook extending from the distal end of the guide device. An exemplary hook can have a shape that is adapted to engage the posterior arch of a vertebra in the cervical spine. The retractor guide can also have a variety of configurations, but in one embodiment the retractor guide is a bar or arm that extends laterally from the guide member and that defines a pathway formed therethrough for receiving a tissue retractor.

In another embodiment, the spinal guide device can be adjustable. In particular, the guide member can be slidably coupled to a housing. For example, the housing can include a bore extending therethrough for receiving the guide member. The spinal guide device can also include a locking mechanism that is coupled to the housing and that is adapted to lock the guide member in a fixed position relative to the housing. In one exemplary embodiment, the proximal end of the guide member can include annular grooves formed therearound and spaced apart from one another, and the locking mechanism can be adapted to engage at least one of the annular grooves to lock the guide member in a fixed position relative to the housing. By way of non-limiting example, the locking mechanism can be a push-button mechanism that is movable between a first position, in which the push-button mechanism engages at least one of the annular grooves formed on the guide member, and a second position, in which the guide member is freely slidable relative to the housing. In an exemplary embodiment, the push-button mechanism is biased to the first position.

In another embodiment, the guide device can include a second positioning element that is adapted to be positioned relative to the guide member, e.g., through the guide member, over the guide member, or adjacent to the guide member. In certain embodiments, the second positioning element can be a sleeve, and the sleeve can include a tapered distal tip that is adapted to extend distally beyond the distal end of the guide member. In other embodiments, the second positioning element or sleeve can be axially adjustable relative to the guide member, and it can also be adapted to removably mate to the guide member to allow an axial position of the second positioning element or sleeve to be fixed with respect to the guide member of the guide device. For example, the sleeve can include threads formed on an external surface thereof for mating with threads formed on an internal surface of the guide member.

A variety of tools for use with a spinal guide device are also provided. For example, a spinal guide system can include a retractor having a proximal end that is adapted to engage the guide member of the guide device, and a distal end that is adapted to be inserted through the retractor guide to retract tissue. The spinal guide system can also include bone preparation tools, such as depth indicators, drills, taps, and awls, for preparing a bone hole in bone. In an exemplary embodiment, the tool has a distal tip with a length that is less than three times a diameter thereof.

A spinal screw is also provided that allows the insertion depth thereof into bone to be adjusted after the screw is implanted and mated to a spinal fixation element. One exemplary spinal screw is a polyaxial screw having a shank and a head formed thereon. The shank includes a distal threaded region and a proximal thread-free region. The proximal thread-free region can include an engagement mechanism formed thereon for allowing the shank to be engaged and rotated into bone after a spinal fixation element, such as a spinal rod, is mated to the head. In one embodiment, the engagement mechanism can be a nut or hexagonal member that is fixedly attached to the shank such that rotation of the nut is effective to rotate the shank.

Methods for using the various tools and devices disclosed herein are also provided.

DETAILED DESCRIPTION OF THE EXEMPLARY EMBODIMENTS

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various spinal tools and devices for use in spinal surgery are provided. A person skilled in the art will appreciate that while the tools and devices are described in connection with the cervical spine, the tools and devices can be adapted for use in other areas of the spine, as well as for use in other surgical procedures.

Figure 1A:
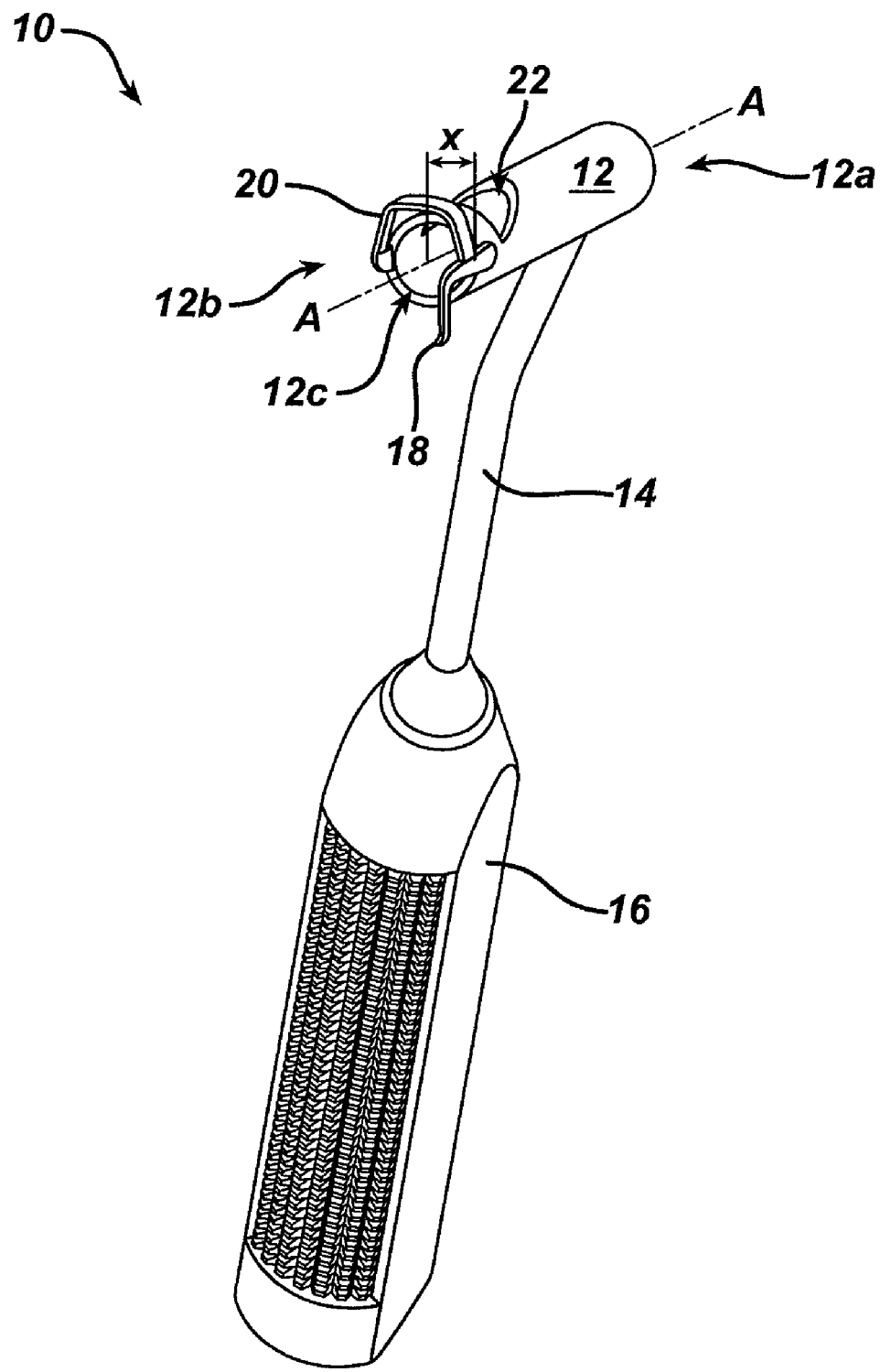
FIG. 1A is side perspective view of a one embodiment guide device.
Figure 1B:
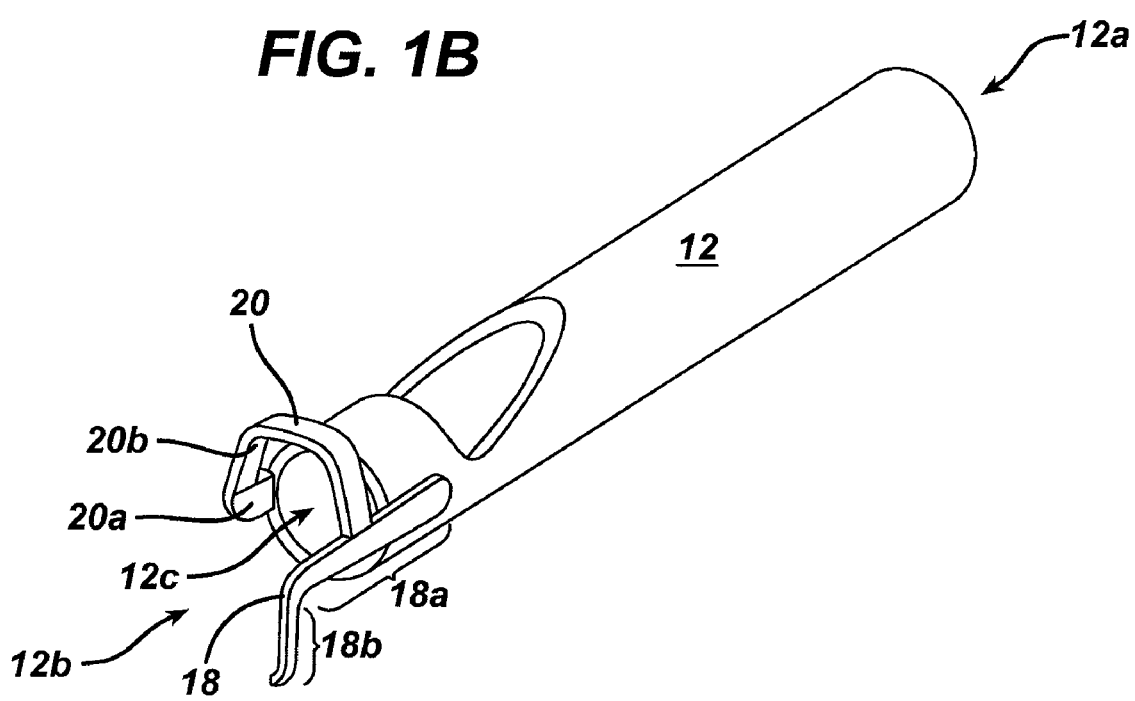
FIG. 1B is a side perspective view of the distal portion of the guide device shown in FIG. 1A.
Figure 1C:
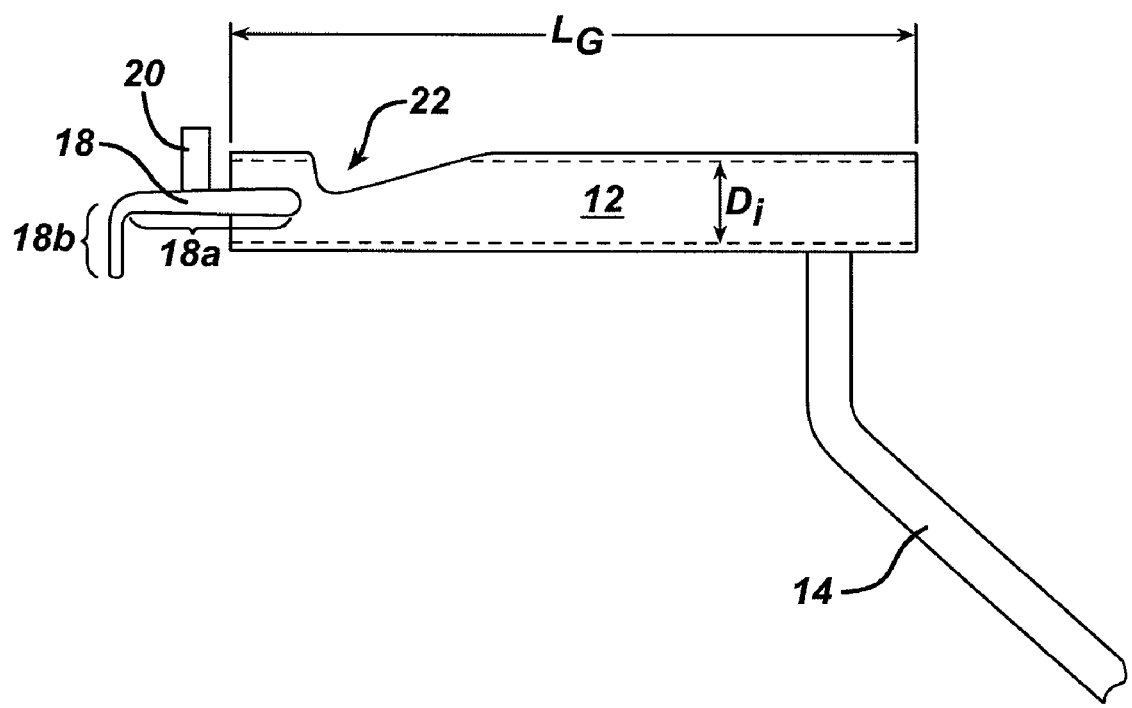
FIG. 1C is a side view of the guide device shown in FIG. 1A.

FIGS. 1A-1C illustrate one embodiment of a guide device 10 for guiding tools and implants to a spinal fixation site. In general, the guide device 10 includes a shaft 14 having a handle 16 formed thereon to facilitate grasping and manipulation of the device 10, and an elongate tubular guide member 12 having a proximal end 12a and a distal end 12b defining an inner lumen 12c extending therebetween. The shaft 14 can be mated to any portion of the guide member 12, but in an exemplary embodiment the shaft 14 is mated to a sidewall of the guide member 12 adjacent to the proximal end 12a, such that the shaft 14 does not interfere with access to the lumen 12c extending through the guide member 12. The guide member 12 can have a variety of configurations, shapes, and sizes, but an exemplary guide member 12 is effective to guide spinal tools and implants to a spinal fixation site. As shown in FIGS. 1A-1C, the guide member 12 is substantially cylindrical.

The guide member 12 can include features to facilitate positioning of the guide member 12 relative to a vertebra. In one embodiment, as shown, the guide member 12 includes a positioning element 18 extending from the distal end 12b thereof. The positioning element 18 can be adapted to engage a vertebra to maintain the guide member 12 in a substantially fixed position relative to the vertebra. In an exemplary embodiment, the positioning element 18 has a shape that facilitates engagement of the posterior arch of a vertebra in the cervical spine, such as the posterior arch of the C1 vertebra in the cervical spine. By way of non-limiting example, the positioning element 18 can be in the form of a hook, as shown in FIGS. 1A-1B. The hook-shaped positioning element 18 can include a proximal portion 18a that extends distally from an outer sidewall of the guide member 12, and a distal portion 18b that extends at an angle relative to the proximal portion 18a such that the distal portion 18b is configured to fit around and engage a vertebra. Such a configuration is particularly advantageous where the positioning element 18 is used to engage the C1 vertebrae, as the hook shape of the positioning element 18, as well as the distance x of the positioning element 18 from a central axis A, can be used to center the guide member 12 relative to the C1 vertebra, and to maintain the guide member 12 in the centered position, as will be discussed in more detail below.

The guide member 12 can also include features to facilitate use of a spinal retractor, or other tool for moving tissue, in connection with the guide member 12. In one embodiment, as shown, the guide member 12 includes a retractor guide 20 that is in the form of an arm or bar that extends radially outward from the distal end 12b of the guide member 12. More particularly, the retractor guide 20 can include a first portion 20a that extends distally from a side of the guide member 12 that is opposite to the positioning element 18, and a second portion 20b that extends transversely relative to the first portion 20a and that connects to the positioning member 18. The second portion 20b can be substantially C-shaped or semi-circular, or it can have any other shape that allows it to be positioned radially outward from the guide member 12 such that a tissue retractor or other device can be inserted directly through the retractor guide 20. A person skilled in the art will appreciate that the retractor guide 20 can have a variety of other configurations, shapes, and sizes, and that it can connect to or be formed on any portion of the guide member 12.

Figure 2:
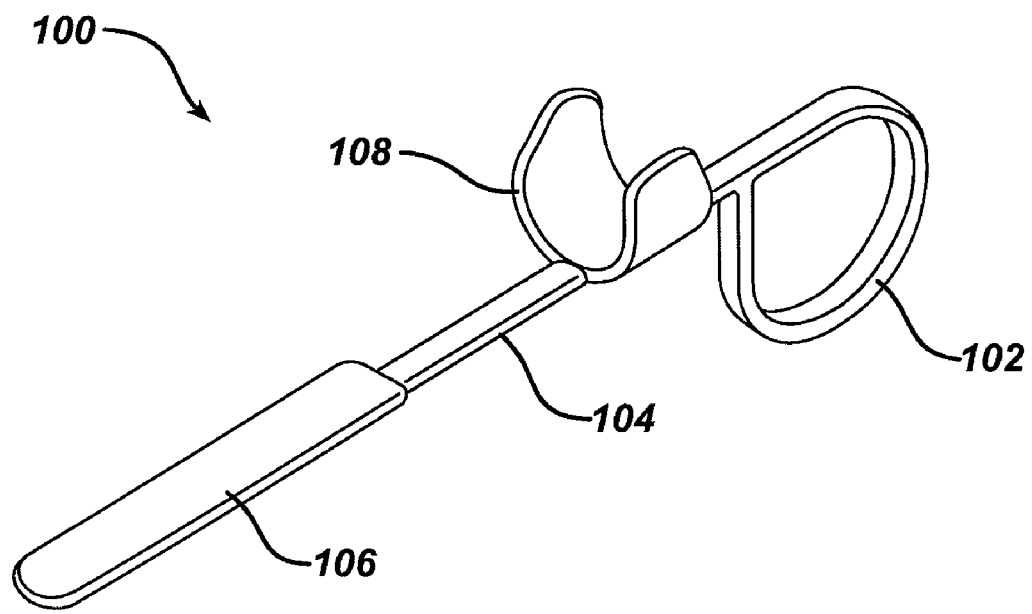
FIG. 2 is a side perspective view of one embodiment of a spinal retractor.

FIG. 2 illustrates one embodiment of an exemplary tissue retractor 100 for use with the retractor guide 20 on the guide device 10 shown in FIGS. 1A-1C. As shown, the tissue retractor 100 includes a proximal handle 102, in the form of a hoop, to facilitate grasping of the device 100, and an elongate shaft 104 having a flattened distal portion 106 that can be used to retract tissue, such as the nerve root in the cervical spine. The tissue retractor 100 can also include a mating element, such as clip 108 shown, that is adapted to removably engage the guide member 12. In use, which will be discussed in more detail below, the distal portion 106 of the tissue retractor 100 is passed external to the guide member 12 and through the retractor guide 20 at an angle to engage tissue. It is then pivoted to move the tissue and cause the clip 108 to engage the guide member 12, thereby holding the tissue out of the way of the lumen 12c in the guide member 12.

Figure 3:
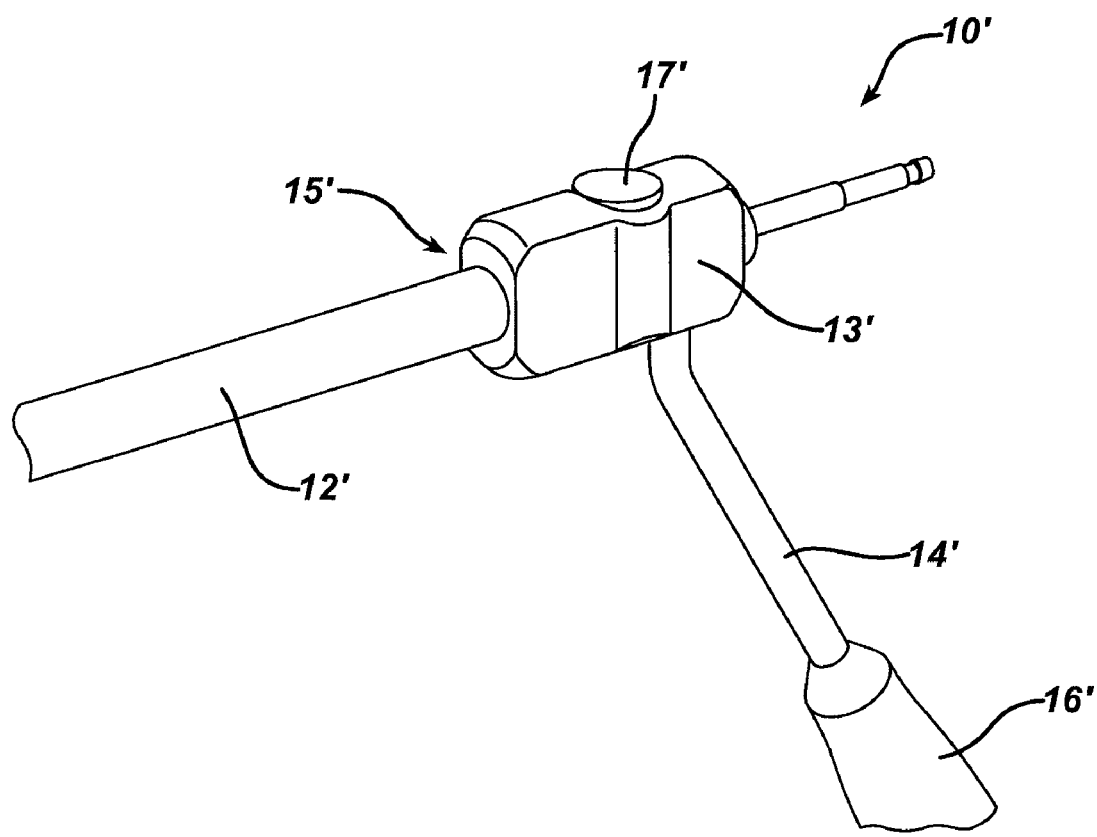
FIG. 3 is a side perspective view of a portion of one embodiment of an adjustable guide device.

In another embodiment, the guide member on the guide device can be adjustable to allow the length of the guide member to be set according to the desired depth of insertion. While various techniques can be used to allow adjustability of the guide device, FIG. 3 illustrates one example of an adjustable design. As shown, the guide member 12', only a portion of which is illustrated, is slidably disposed through a housing 13' on the guide device 10'. The housing 13' is attached to the elongate shaft 14', which includes a handle 16' for grasping and manipulating the device 10'. The housing 13' can have a variety of configurations, but as illustrated the housing 13' has a substantially rectangular shape with a bore 15' extending therethrough for slidably receiving the guide member 12'. The housing 13' also includes a locking mechanism for retaining the guide member 12' in a fixed position relative to the housing 13'. While virtually any technique can be used to lock the guide member 12' in a fixed position, in the illustrated embodiment the locking mechanism is in the form of a push-button 17'. The push-button 17' has a portion that extends into and across the bore 15' in the housing 13', and that has an oblong bore (not shown) formed therein for receiving the guide member 12'. When the push-button 17' is in a first position, the push-button 17' is effective to engage the guide member 12'. In an exemplary embodiment, the proximal portion of the guide member 12' includes grooves formed therearound to facilitate engagement thereof by the push-button 17'. The housing 13' can also include a biasing element, such as a spring (not shown), disposed therein for biasing the push-button 17' toward the first position. When the push-button 17' is depressed into a second position, the guide member 12' is free to slidably move relative to the oblong bore on the push-button 17', and relative to the housing 13'. As a result, the guide member 12' can be adjusted to have a length that corresponds to a desired insertion depth. A person skilled in the art will appreciate that the guide member 12' can be adjusted using a variety of other techniques, and that it does not need to be slidably disposed through a housing.

Figure 4A:
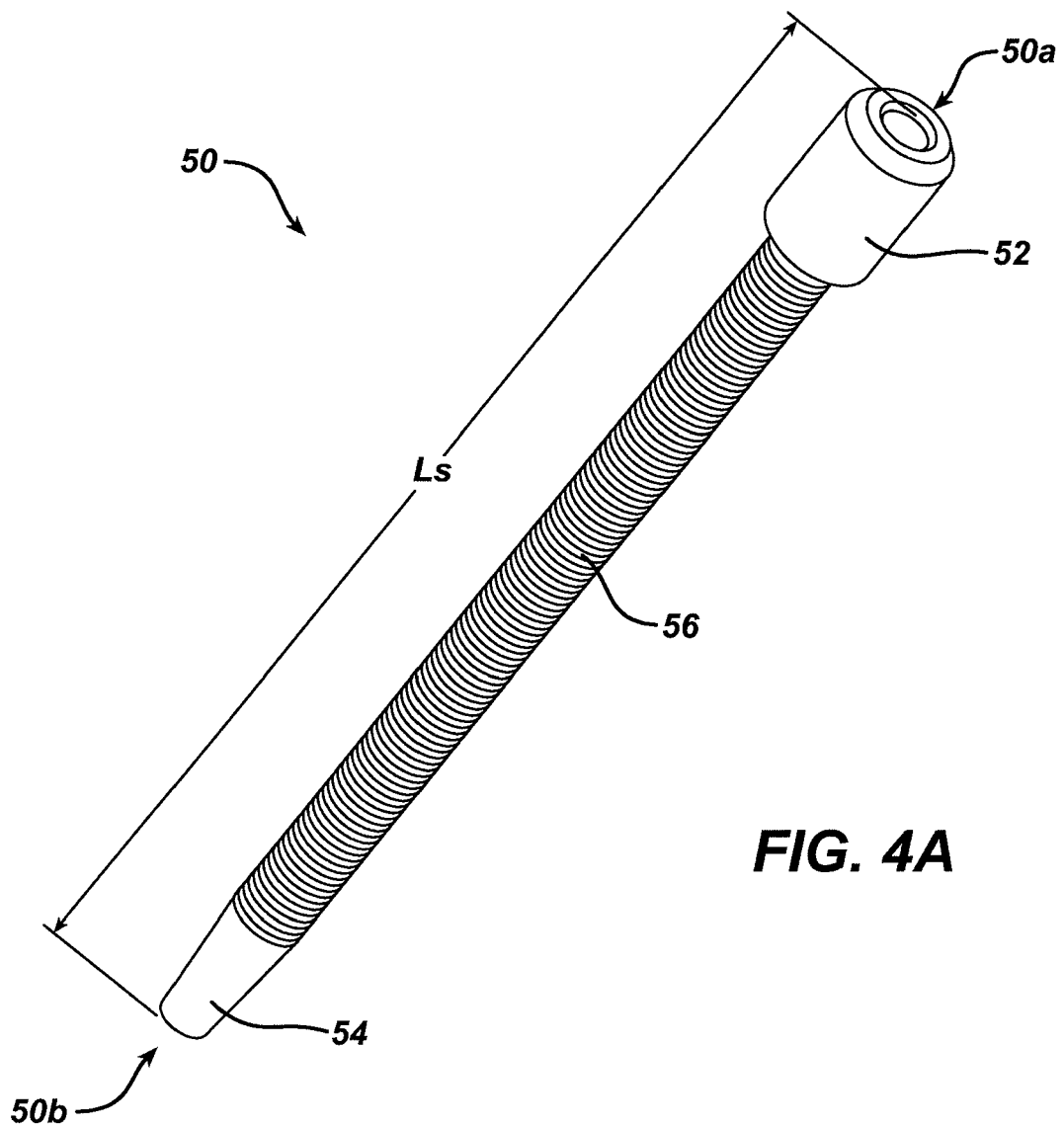
FIG. 4A is a side perspective view of one embodiment of a sleeve for use with a guide device.
Figure 4B:
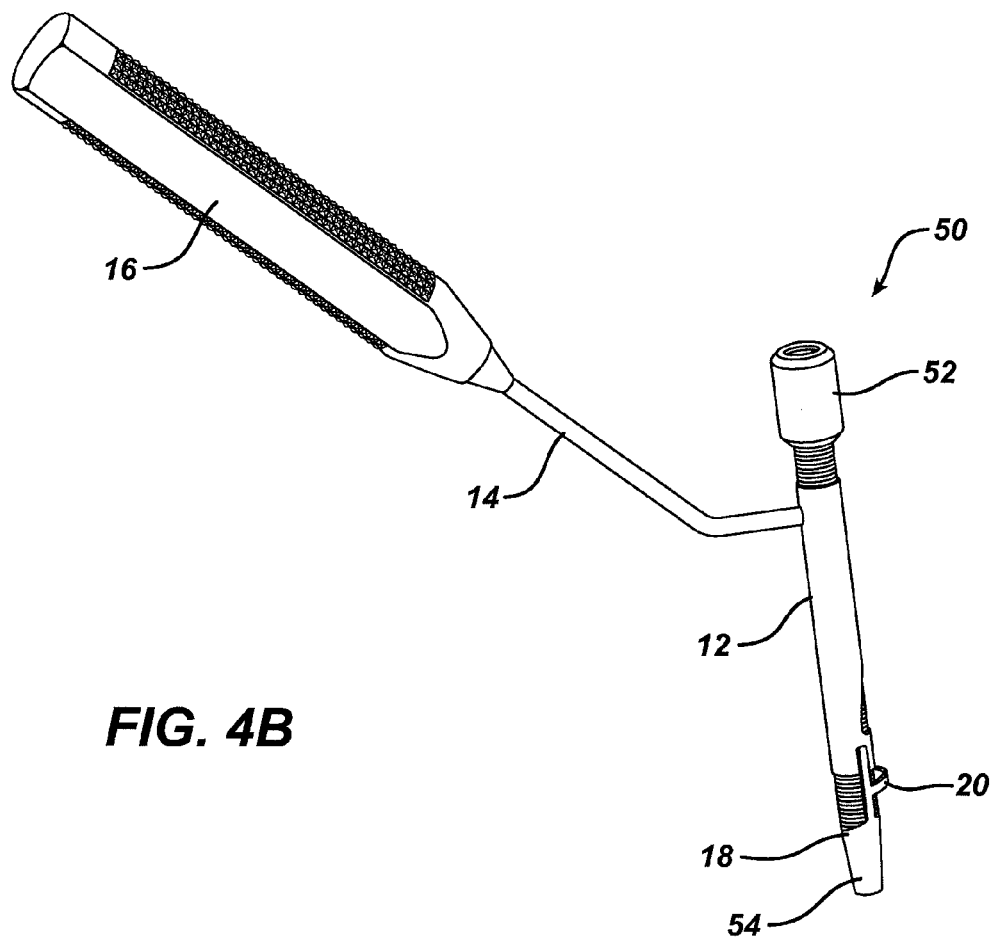
FIG. 4B is a side perspective view of the sleeve shown in FIG. 4A inserted through the guide device shown in FIG. 1A.

FIGS. 4A-4B illustrate yet another embodiment of a device for use in spinal surgery. Referring first to FIG. 4A, a second positioning element, which is in the form of a sleeve 50, is shown for use with the guide device 10. In general, the sleeve 50 is in the form of an elongate tubular member having proximal and distal ends 50a, 50b. The sleeve 50 has an outer diameter $D_o$ that is smaller than an inner diameter $D_i$ of the guide member 12 (shown in FIG. 1C) to allow the sleeve 50 to be received within the guide member 12. The sleeve 50 can, however, include an enlarged head 52 formed on the proximal end 50a that is adapted to abut the proximal end 12a of the guide member 12 to prevent the sleeve 50 from passing completely through the guide member 12. The sleeve 50 can also include a distal tapered tip 54 that is adapted to extend distally beyond the distal end 12b of the guide member 12. Accordingly, the sleeve 50 can have a length $L_s$ that is greater than a length $L_g$ of the guide member 12 (shown in FIG. 1C) to allow the distal tapered tip 54 to extend through and beyond the distal end 12b of the guide member 12.

The sleeve 50 can also be adapted to removably mate with the guide member 12, and it could also be axially adjustable relative to the guide member. While various techniques can be used to provide a mating configuration, FIG. 4A illustrates threads 56 formed on the outer surface of the sleeve 50 for mating with corresponding threads (not shown) formed on the inner surface of the guide member 12. In use, the sleeve 50 can be threaded into the guide member 12, as shown in FIG. 4B, to reduce the diameter of the guide member 12. The reduced diameter is effective to guide bone preparation tools, such as drills, taps, and awls, through the guide device 10. The distal tapered tip 54 can also function to protect surrounding tissue from the tools that are inserted through the guide member 12. The sleeve 50 can also function to maintain the guide device 10 in a substantially fixed position relative to bone. In particular, the sleeve 50 can be fully threaded into the guide member 12 such that the distal tapered tip 54 of the sleeve 50 extends distally beyond the distal end 12b of the guide member 12, shown in FIG. 4B, to abut against the bone and thus hold the guide member 12 in position relative to the bone. The distal tip 54 can also function in combination with the positioning element 18 to maintain the guide member 12 in a substantially fixed position. In particular, as the positioning element 18 engages or pulls on a portion of the bone, the distal tip 54 can abut against or push on the bone. The opposed push-pull forces thus counter each other to substantially prevent movement of the guide member 12.

A person skilled in the art will appreciate that a variety of other techniques can be used to maintain the guide member 12 in a substantially fixed position, and that the positioning element can have a variety of other configurations. Moreover, the positioning element can be configured to be disposed through, over, or adjacent to the guide member 12. By way of non-limiting example, the retractor 100 can function in place of the sleeve 50. For example, the retractor 100 could be advanced along guide member 12, manipulated to retract the nerve, and then advanced against bone to counter the pulling forces applied to the bone by the positioning element 18. The clip 108 on the retractor 100 can then be used to lock the retractor 100 relative to the guide member 12, or some other locking mechanism can be used to maintain the position of the retractor 100 relative to the guide member 12. By way of non-limiting example, other exemplary locking mechanisms include a screw, a ratchet, a clamp, etc.

Figure 5A:
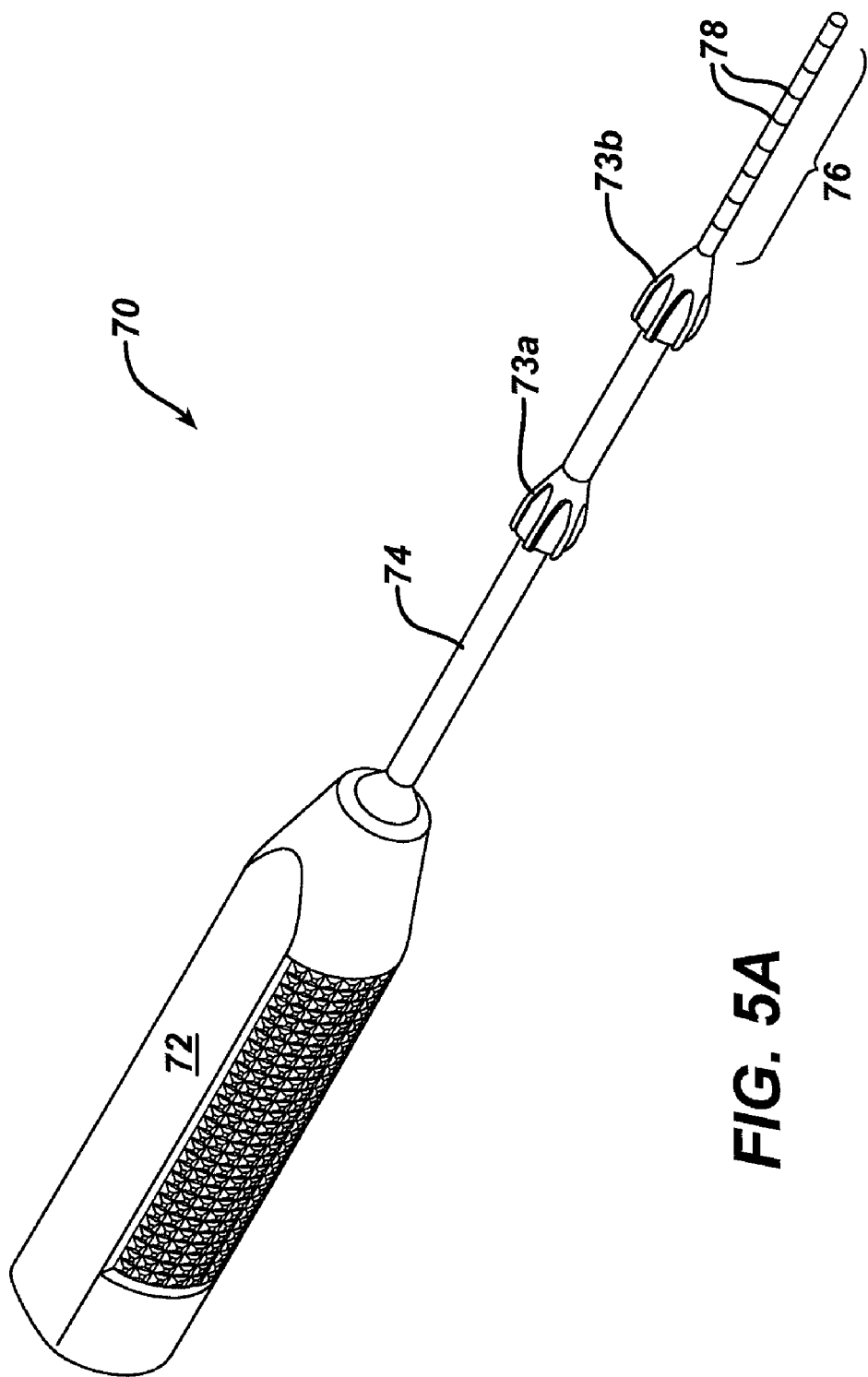
FIG. 5A is a side perspective view of one embodiment of a depth indicator device.
Figure 5B:
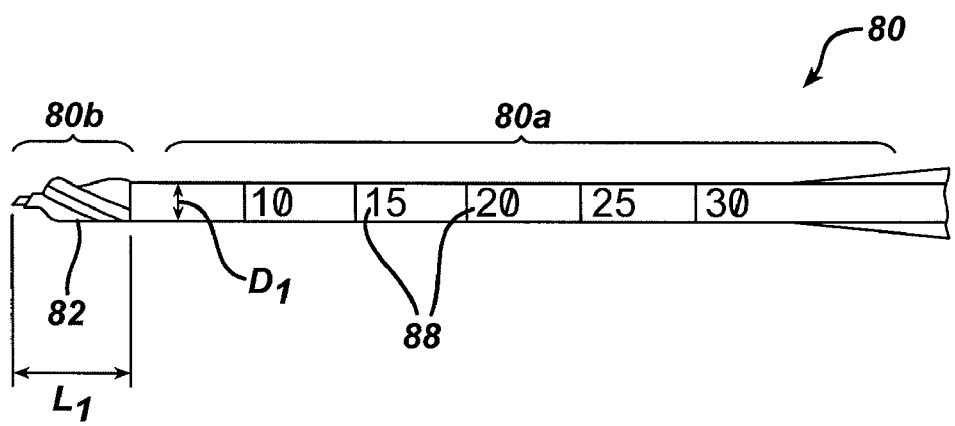
FIG. 5B is a side view of one embodiment of a drill tip for drilling a hole in bone.
Figure 5C:
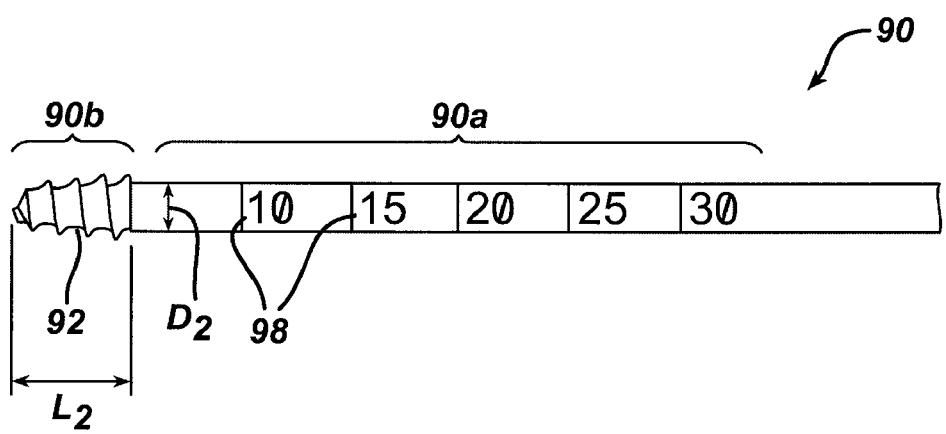
FIG. 5C is a side view of one embodiment of a tap for forming threads within a bone hole.

Various tools for use in preparing bone are also provided, as shown in FIGS. 5A-5C. While the tools are described in combination with guide device 10, a person skilled in the art will appreciate that the tools can be used with a variety of other devices and/or for a variety of other purposes.

FIG. 5A illustrates one embodiment of a depth indicator tool 70 that can be used to measure the depth of a bone hole. As shown, the tool 70 includes a handle 72 and an elongate shaft 74 extending from the handle 72. A distal tip portion 76 is attached to the elongate shaft 74 and it is adapted to be disposed within a bone hole to measure a depth of the bone hole. The distal tip portion 76 can be removable to allow tips having various other configurations to be used with the handle 72. The distal tip portion 76 can also include markings 78 formed thereon and spaced an equal distance apart from one another to allow measurement of the insertion depth. In certain exemplary embodiments, the markings 78 can be in the form of radio-opaque grooves such that the markings 78 are visible by x-ray imaging.

As is further shown in FIG. 5A, the depth indicator tool 70 can also include a feature to axially align the tool 70 when inserted through a guide device, such as guide device 10. While various techniques can be used to achieve axial alignment, in the illustrated embodiment the shaft 74 of the depth indicator tool 70 includes two centering mechanisms 73a, 73b disposed around the shaft 74 and spaced a distance apart from one another. Each centering mechanism 73a, 73b has a diameter that is larger than a diameter of the shaft 74, and each centering mechanism 73a, 73b has a substantially hexagonal shape. In use, when the depth indicator tool 70 is disposed through the guide member 12, the centering mechanisms 73a, 73b slidably engage the inner wall of the guide member 12 to axially align the shaft 74 and distal tip portion 76 with the guide member 12. The hexagonal shape of the centering mechanisms 73a, 73b prevents the centering mechanisms 73a, 73b from forming a seal with the guide member 12 to thereby allow easy movement of the depth indicator tool 70 relative to the guide member 12. A person skilled in the art will appreciate that the tool 70 can include any number of centering mechanisms 73a, 73b, or other devices for facilitating axial alignment, and that the centering mechanisms 73a, 73b can have virtually any shape and size. The centering mechanisms 73a, 73b can also be adapted for use with sleeve 50, but in an exemplary embodiment the tool 70 does not include centering mechanism 73a, 73b when used in combination with the sleeve 50, which functions to axial align the tool 70 with the guide member 12.

FIGS. 5B and 5C illustrate another embodiment of bone preparation tool 80, 90. In FIG. 5B the tool 80 is in the form of a drill bit for forming a hole in bone, and in FIG. 5C the tool 90 is in the form of an awl for preparing a bone hole. While not shown, the drill bit 80 and/or awl 90 can be fixedly attached to a handle, such as handle 72 shown in FIG. 5A, or they can be removably attached to a handle, and interchangeable with each other and/or the distal tip portion 76 of the depth indicator tool 70 shown in FIG. 5A. The drill bit 80 and awl 90 can also include features, such as the centering mechanisms 73a, 73b shown in FIG. 5A, to facilitate axial alignment with a guide device, such as guide device 10. As is further shown in FIGS. 5B and 5C, the drill bit 80 and awl 90 can also include markings or indicia 88, 98 formed thereon, e.g., on the proximal portion 80a, 90a thereof, for indicating an insertion depth of the device 80, 90, as previously described above with respect to the depth indicator tool 70 of FIG. 5A. A person skilled in the art will appreciate that the drill bit 80 and awl 90 can have a variety of others configurations and they can include a variety of other features to facilitate use thereof.

As is further shown in FIGS. 5B and 5C, the drill bit 80 and the awl 90 also include a cutting element 82, 92 formed thereon. In particular, the drill bit 80 includes flutes 82 for forming a hole in bone, and the awl 90 includes threads 92 for forming threads within a bone hole. In an exemplary embodiment, as shown, the cutting element 82, 92 is only formed on a distal-most portion 80b, 90b of each device 80, 90. More particularly, the cutting element 82, 92 can have a length $L_1$, $L_2$ that, in an exemplary embodiment, is less than three times the diameter $D_1$, $D_2$ of the shaft of the device 80, 90, and more preferably that is less than about 10 mm. Such a configuration is particularly advantageous in that it prevents potential damage to tissue surrounding the surgical site, as the distal-most portion 80b, 90b of the tool 80, 90 will only be exposed during initial insertion.

Figure 6:
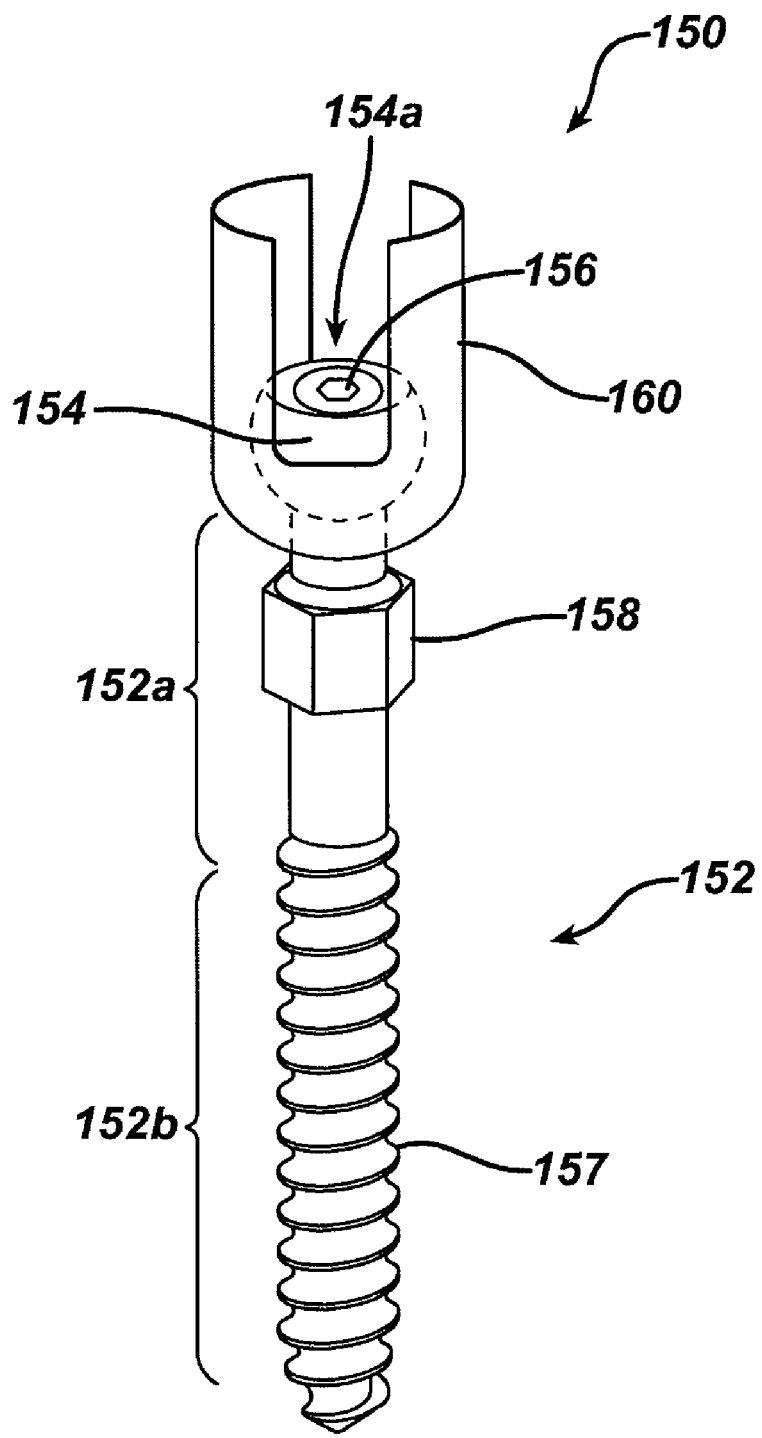
FIG. 6 is a side perspective view of one embodiment of a bone screw.

In another embodiment, an adjustable bone screw 150 is provided, as shown in FIG. 6. While the bone screw 150 can be used in a variety of surgical applications, in an exemplary embodiment the bone screw 150 is used in the cervical spine with various other tools and devices disclosed herein. As shown, the bone screw 150 includes a shank 152 and a head 154 formed thereon. The head 154 can have various shapes and sizes, but in certain exemplary embodiments it is substantially spherical such that it is adapted to rotatably sit within a receiver member 160 to allow polyaxial movement of the shank 152 relative to the receiver member 160. The head 154 can also include a flattened proximal end 154a with a recess 156 or other mating element formed therein for allowing engagement of the head 154 by a driver tool for driving the bone screw 150 into bone.

The shank 152 of the bone screw 150 can also have a variety of configurations, but in an exemplary embodiment it includes a proximal portion 152a that is thread-free, and a distal portion 152b with threads 157 formed thereon. The thread-free proximal portion 152a can include an engagement mechanism 158 formed thereon or mated thereto. The engagement mechanism 158 can have virtually any configuration, but it one exemplary embodiment it is in the form of a hex nut that is disposed around the shank 152, as shown. The hex nut 158 allows the shank 152 to be engaged with a driver tool and threaded into or out of bone after a spinal fixation element, such as a spinal rod, is disposed within the receiver member 160, as the spinal rod will necessarily prevent access to the recess 156. A person skilled in the art will appreciate that a variety of other techniques can be used to facilitate engagement of the shank 152 after the bone screw 150 is implanted and the recess 156 for driving the bone screw 150 into bone is no longer accessible. Moreover, the bone screw 150 can have a variety of other configurations and it can be used with a variety of receiver members or other devices for mating a spinal fixation element to the bone screw 150.

Figure 7A:
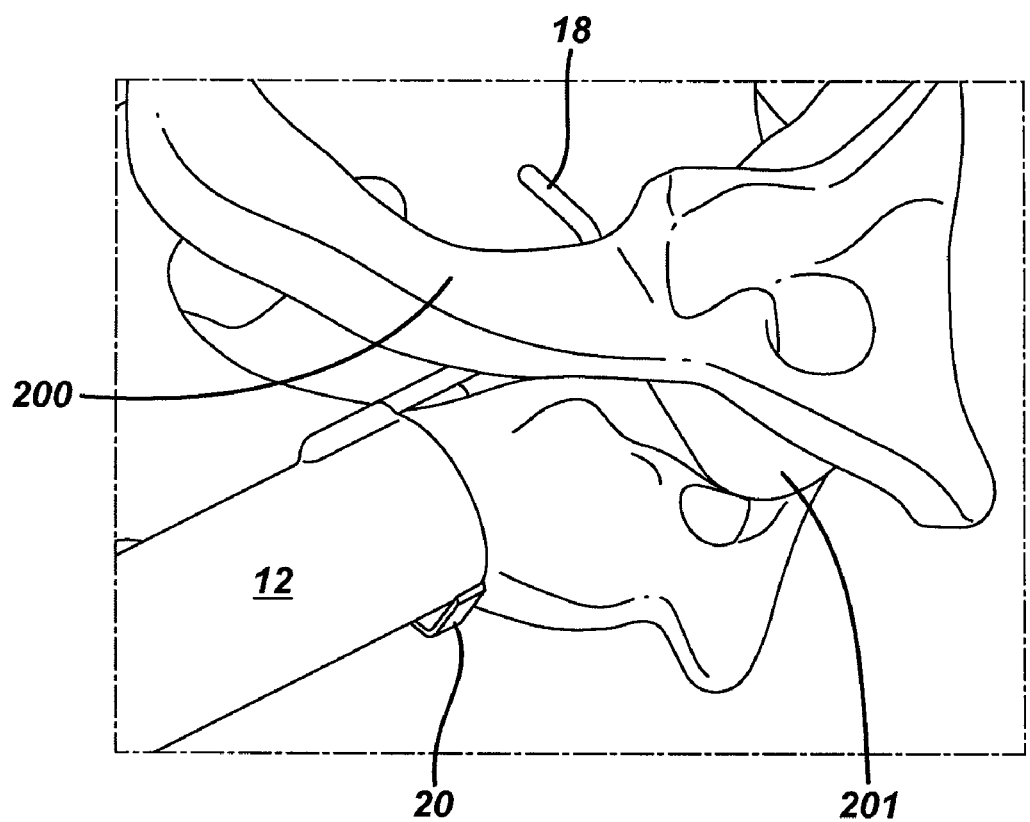
FIG. 7A is an illustration showing a portion of the guide device shown in FIG. 1A engaging a vertebra.
Figure 7B:
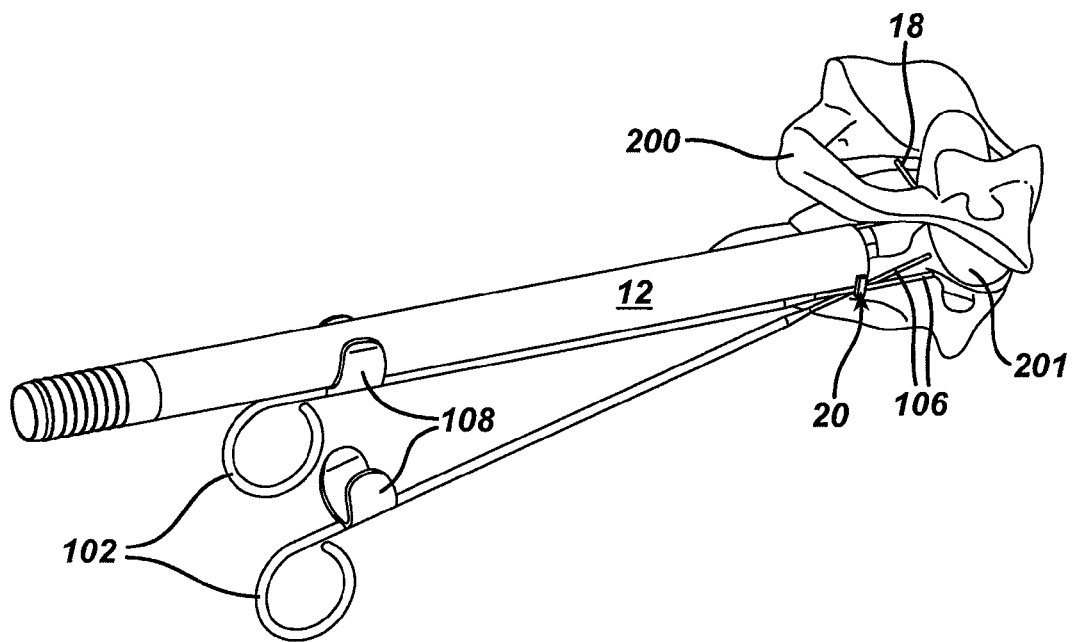
FIG. 7B is an illustration showing the spinal retractor of FIG. 2 in two positions as used in conjunction with the guide device shown in FIG. 7A.

FIGS. 7A-7B illustrate an exemplary technique for preparing a bone hole and implanting a bone screw using the various exemplary tools and devices disclosed herein. FIG. 7A illustrates a portion of a C1 vertebra in the cervical spine. The surgical site is accessed using standard techniques known in the art, and the guide device 10 is introduced into the surgical site. Where an adjustable guide device 10' is used, the length of the guide device 10' can be adjusted as desired either before or after insertion. The positioning element 18 on the guide member 12 of the guide device 10 is then positioned around the posterior arch 200 of the C1 vertebra to engage the vertebra and maintain the guide device 10 in a substantially fixed position relative to the vertebra. Due to the distance x (shown in FIG. 1A) between the positioning element 18 and the central axis A of the guide member 12, the positioning element 18 can be effective to center the guide member 12 over the lateral mass 201 of the vertebrae. The tissue retractor 100 can then be passed along the exterior of the guide member 12 and inserted through the retractor guide 20. As shown in FIG. 7B the tissue retractor 100 is inserted in a first position in which the handle 102 is spaced apart from the guide member 12 and the distal end 106 of the tissue retractor 100 extends into the pathway of the guide member 12. The tissue retractor 100 is then rotated to a second position to retract tissue, such as the nerve root, away from the pathway of the guide member 12 and to mate to the guide member 12 using clip 108. As previously described, the tissue retractor 100 can be advanced against the lateral mass 102 of the vertebra to counter the forces applied by the positioning element 18, and thereby substantially prevent movement of the guide member 12 relative to the vertebra.

Figure 8:
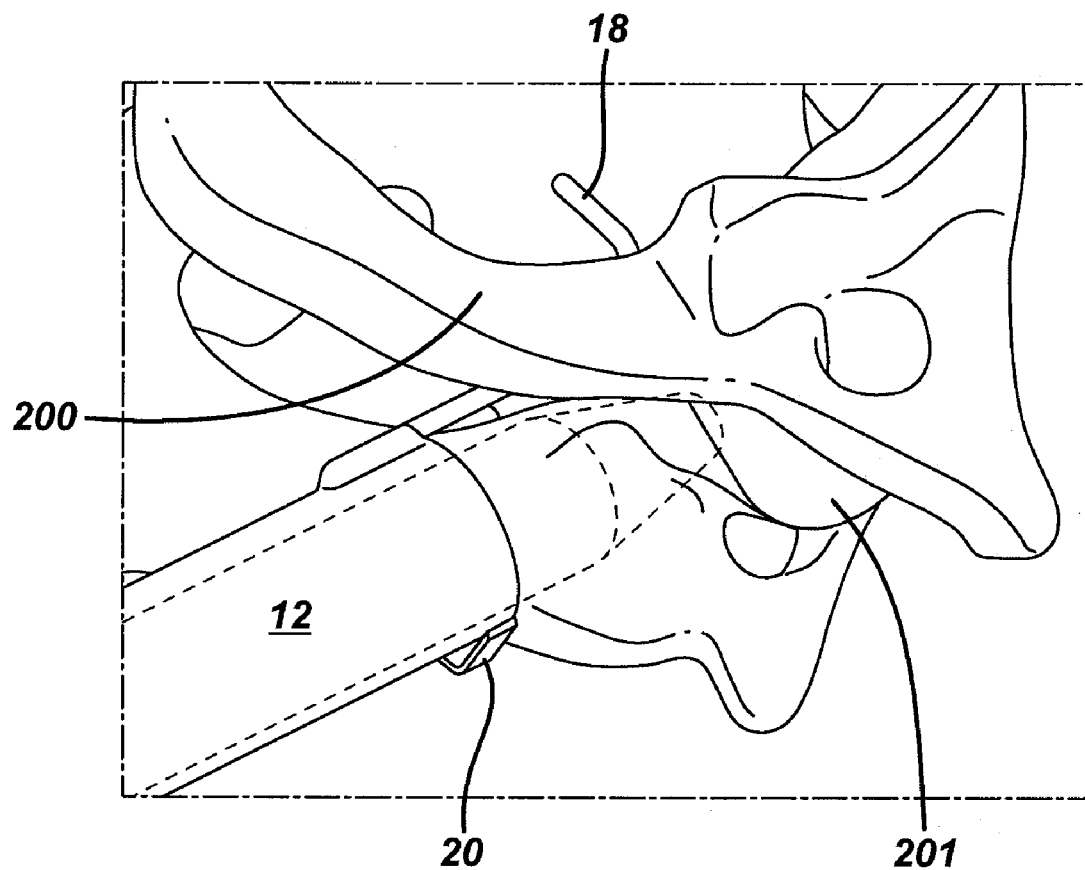
FIG. 8 is an illustration showing a portion of the guide device shown in FIG. 1A engaging a vertebra and having the sleeve shown in FIG. 4A disposed therethrough.

In another embodiment, shown in FIG. 8, the sleeve 50 can be used in combination with the guide device 10. In particular, the guide device 10 would be oriented to the spine as described above, with positioning element 18 positioned around posterior arch 200. The sleeve 50 would then be advanced through guide member 12 such that the tapered end 54 would abut against the lateral mass 201 of the vertebra, as shown. As a result, the sleeve 50 would push against the bone, counter the pulling force applied by the positioning element 18, thereby substantially preventing movement of the guide member 12 with respect to the vertebra. As a result, the axis A of guide member 12 would be substantially locked in place relative to the anatomy and it would not be able to pivot about positioning element 18.

Once the guide device 10 is properly positioned, either with or without sleeve 50, the various bone preparation tools 70, 80, 90 can then be inserted through the guide member 12 to form and prepare a hole in the vertebra. Once the bone hole is prepared, a bone screw, such as screw 150, can be inserted through the guide member 12 and driven into the bone hole using a driver tool (not shown). The guide device 10 is then removed and a spinal fixation element, such as a spinal rod (not shown), can then be attached to the receiver member 160 on the bone screw 150. If necessary, a driver device, such as a wrench, can be used to engage the engagement mechanism 158 on the bone screw 150 to adjust the depth of insertion of the bone screw 150 into the bone hole.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A spinal guide system, comprising:
an elongate tube having opposed proximal and distal open ends;

a positioning element extending distally from a sidewall of the distal end of the elongate tube, the positioning element having a distal end configured to engage a vertebra to position the elongate tube relative to the vertebra; and a c-shaped retractor guide with first and second terminal ends directly attached to opposite sides of the elongate tube, and with a mid-portion spaced radially outward from the elongate tube such that the retractor guide defines a pathway configured to slidably receive a retractor for retracting tissue adjacent the vertebra.

2. The spinal guide system of claim 1, wherein the distal end of the positioning element extends distally beyond the retractor guide.

3. The spinal guide system of claim 1, wherein the mid-portion of the retractor guide has a longitudinal axis that is substantially perpendicular to a longitudinal axis of the elongate tube.

4. The spinal guide system of claim 1, wherein the positioning element has a first portion extending distally from the sidewall of the distal end of the elongate tube and a second portion extending at an angle from the first portion.

5. The spinal guide system of claim 1, further comprising a sleeve configured to be positioned relative to and advanced beyond the distal end of the elongate tube.

6. The spinal guide system of claim 1, further comprising a depth indicator tool configured to be disposed through the elongate tube and having a plurality of indicia formed thereon.

7. The spinal guide system of claim 1, further comprising a spinal screw configured to be disposed through the elongate tube and to be implanted in bone.

8. A spinal guide system, comprising:
an elongate shaft having a handle coupled to a proximal end thereof and a guide member coupled to a distal end thereof, the guide member including
an elongate tube having opposed proximal and distal ends with an inner lumen extending therebetween, the distal end of the elongate shaft being coupled to a sidewall of the elongate tube adjacent the proximal end of the elongate tube,
a positioning element coupled to and extending distally beyond the distal end of the elongate tube, and
a retractor guide coupled to the distal end of the elongate tube, the retractor guide defining an opening extending between the retractor guide and an exterior surface of a sidewall of the elongate tube, the opening being configured to slidably receive a retractor between the retractor guide and the exterior surface of the sidewall to retract tissue adjacent a vertebra engaged by the positioning element.

9. The spinal guide system of claim 8, wherein the retractor guide is c-shaped and has opposed ends mated to opposed sides of the elongate tube.

10. The spinal guide system of claim 8, wherein the positioning element has a first portion extending distally from a sidewall of the distal end of the elongate tube and a second portion extending at an angle from the first portion.

11. The spinal guide system of claim 8, wherein a longitudinal axis of the elongate tube is offset at an angle from a longitudinal axis of at least a distal portion the elongate shaft.

12. The spinal guide system of claim 11, wherein the longitudinal axis of the elongate tube is substantially perpendicular to the longitudinal axis of at least the distal portion of the elongate shaft.

13. The spinal guide system of claim 8, further comprising a retractor configured to be slidably received in the opening.

14. The spinal guide system of claim 13, wherein a longitudinal axis of the elongate tube is substantially parallel to a longitudinal axis of the retractor when the retractor is slidably received in the opening.

15. The spinal guide system of claim 13, wherein the retractor includes a mating element configured to removably engage the sidewall of the elongate tube when a distal end of the retractor extends distally beyond the distal end of the elongate tube.

16. The spinal guide system of claim 15, wherein the mating element includes a c-shaped clip.

17. A spinal guide system, comprising:
an elongate tube having opposed proximal and distal ends;
a positioning element having a first end directly mated to a sidewall of the elongate tube and a second end extending distally beyond the distal end of the elongate tube; and
a retractor guide extending between the elongate tube and the positioning element with a first terminal end of the retractor guide being attached to the positioning element and a second terminal end of the retractor guide being attached to the distal end of the elongate tube.

18. The spinal guide system of claim 17, wherein the elongate tube includes at least one window formed therein adjacent to the distal end thereof.

19. The spinal guide system of claim 17, further comprising a sleeve configured to be positioned relative to and advanced beyond the distal end of the elongate tube.

* * * * *